US00PP37012P2

(12) United States Plant Patent
Witney

(10) Patent No.: US PP37,012 P2
(45) Date of Patent: Oct. 14, 2025

(54) ***PERSEA AMERICANA* PLANT NAMED 'BeeOne'**

(50) Latin Name: *Persea americana Mill.*
Varietal Denomination: BeeOne

(71) Applicant: Group Editors Company (Pty) Ltd, George (ZA)

(72) Inventor: Guy Witney, George (ZA)

(73) Assignee: GROUP EDITORS COMPANY (PTY) LTD, George (ZA)

( * ) Notice: Subject to any disclaimer, the term of this patent is extended or adjusted under 35 U.S.C. 154(b) by 0 days.

(21) Appl. No.: 18/955,409

(22) Filed: Nov. 21, 2024

(51) Int. Cl.
*A01H 5/08* (2018.01)
*A01H 6/52* (2018.01)

(52) U.S. Cl.
USPC ..... Plt./200

(58) Field of Classification Search
USPC ..... Plt./200
CPC . A01H 5/08; A01H 5/00; A01H 6/525; A01H 6/52
See application file for complete search history.

(56) References Cited

U.S. PATENT DOCUMENTS

PP139 P * 8/1935 Hass ..... Plt./200
PP1,967 P * 8/1960 Reed ..... Plt./200
PP14,238 P3 * 10/2003 Bergh ..... A01H 6/52 Plt./200
PP21,099 P3 * 6/2010 Joubert ..... A01H 6/52 Plt./200
PP26,648 P2 * 4/2016 Zaiger ..... A01H 6/7454 Plt./190

* cited by examiner

*Primary Examiner* — June Hwu
(74) *Attorney, Agent, or Firm* — Sterne, Kessler, Goldstein &Fox P.L.L.C.

(57) ABSTRACT

The present invention introduces a novel and distinct variety of *Persea americana* Mill., named 'BeeOne', which emerged from a chance seedling discovered in the Western Cape of South Africa, with commendable commercial traits, including late maturation, thick green skin, and characteristics from both the Mexican and Guatemalan horticultural traits. The traits of 'BeeOne' have been systematically documented from 2018 to the present. Key distinguishing features of 'BeeOne' include its very late ripening and obovate fruit shape, which possesses a notably thick, highly pebbled skin. The fruit is dark green with a flattened base, offering an excellent shelf life and a creamy/nutty flavor profile, complemented by a favorable pulp-to-seed ratio. The tree shape of 'BeeOne' is characterized as upright to moderately spreading, featuring one to three central leaders, which enhances its suitability for high-density planting and interplanting alongside A-flower types, ensuring effective cross-pollination.

8 Drawing Sheets

Genus and species: *Persea americana* Mill.
Variety denomination: 'BeeOne'.

BACKGROUND OF THE VARIETY

The present invention relates to a new and distinct variety of avocado tree (*Persea americana* Mill.) and hereinafter referred to by its variety denomination 'BeeOne'.

The variety was first cultivated in the applicant's nursery at Great Brak Avos, Great Brak River, Western Cape, South Africa and originated by means of a chance seedling unknown cross by the inventor during reconnaissance at the premises of the applicant's owned farm in Leeukloof, Western Cape, Republic of South Africa.

Asexual reproduction of the 'BeeOne' plant at the company commercial nursery in Great Brak River has shown that the unique features thereof are stable and reproduced true to type in successive generations of asexual reproduction by means of grafting.

SUMMARY OF THE VARIETY

The present invention constitutes a new and distinct variety of *Persea americana* Mill. which originated from a chance seedling as detailed herein below.

Dr Guy Witney, a consultant of the applicant was alerted to a chance seedling growing on the premises of one of the farm homes on the applicant's Leeukloof Farm. This tree had typical seedling characteristics including a long branchless trunk, terminating in a high branched crown with a moderate crop of fruit in the canopy. Although the parentage of the new variety is not known, it was determined that the fruit had typical Mexican X Guatemalan avocado race characteristics and good commercial qualities including an excellent pulp to seed ratio, excellent organoleptic qualities, with late maturity and a thick green skin.

Budwood was collected from the tree before it was removed for orchard development and the budwood used to propagate 5 trees. Four trees were propagated on the clonal avocado rootstock Dusa™ in the nursery; and one was topworked to Dusa™ rootstock in the field. The tree and fruit horticultural characteristics have been recorded from 2018 to date.

All colors are described according to The Royal Horticultural Society (R.H.S.) Colour Chart, 1st edition, 1966, except where general color terms of ordinary significance are used or indicated otherwise.

The following traits have been repeatedly observed and are determined to be the unique characteristics, under the local evaluation conditions, of the 'BeeOne' plant. These characteristics in combination distinguish 'BeeOne' as a new and distinct *Persea americana* Mill. variety.

'BeeOne' has a very late ripening obovate fruit shape with a very thick skin and highly pebbled skin texture. The variety has a fruit of dark green color with a flattened fruit base. The fruit has a long shelf-life with a good creamy/nutty taste and has a very favorable pulp to seed ratio. The typical tree shape of 'BeeOne' is upright to moderately spreading with one 1-3 central leaders. This shape lends itself to high density planting and interplanting as a B-flower type with demonstrated strong/cross pollination of A-flower types.

Fruit of the new *Persea americana* Mill. variety 'BeeOne' is readily distinguishable from the most closely related, known variety 'Reed' (described under U.S. Plant Pat. No. 1,967). In this regard, 'BeeOne' has fruit of a obovate shape with a very thick, highly pebbled skin and pronounced lenticels with a dark glossy green skin having prominent yellow flecks. This can be compared to the round fruit of 'Reed' having a thick, lightly pebbled skin of dark glossy color with slight yellow flecks. The pedicel of 'BeeOne' is attached centrally on the highest point or may be slightly offset to one side, whereas the pedicel attachment is generally centered at the highest point of the fruit of 'Reed'. The distal end of the fruit of 'BeeOne' has a slightly flattened 30° offset plane, 3-5 centimeters (cm) in diameter on the distal end of the fruit which is sometimes moderately russeted; whereas the fruit of 'Reed' has a small circular dimple on the distal end of the fruit. The pulp to seed ratio of 'BeeOne' is excellent (average 4.6:1 by weight) with a dark brown seed coat at maturity and a fleshy colored seed. In comparison, 'Reed' has a moderate pulp to seed ratio with a dark brown seed coat at maturity but with a large fleshy colored seed. The fruit of 'BeeOne' has a creamy and nutty taste with a long shelf-life as compared to the creamy taste of 'Reed' with a moderate shelf-life.

'BeeOne' has dark green leaves (near group 139A) with undulate leaf margins. The upper epidermis is slightly glossy. This can be distinguished from the highly glossy upper epidermis of 'Reed'. In addition, 'BeeOne' has dark reddish purple new flush growth with dull to slight gloss as compared to the bronze to light green new flush leaves with highly glossy upper leaf surfaces of 'Reed'.

'BeeOne' is a B-flower type with demonstrated strong/cross pollination of A-flower types, whereas 'Reed' is of the A-flower type.

BRIEF DESCRIPTION OF THE DRAWINGS

The accompanying drawings are color photographs of the new avocado plant 'BeeOne' during December 2023 to September 2024.

DETAILED BOTANICAL DESCRIPTION

Figure 1:
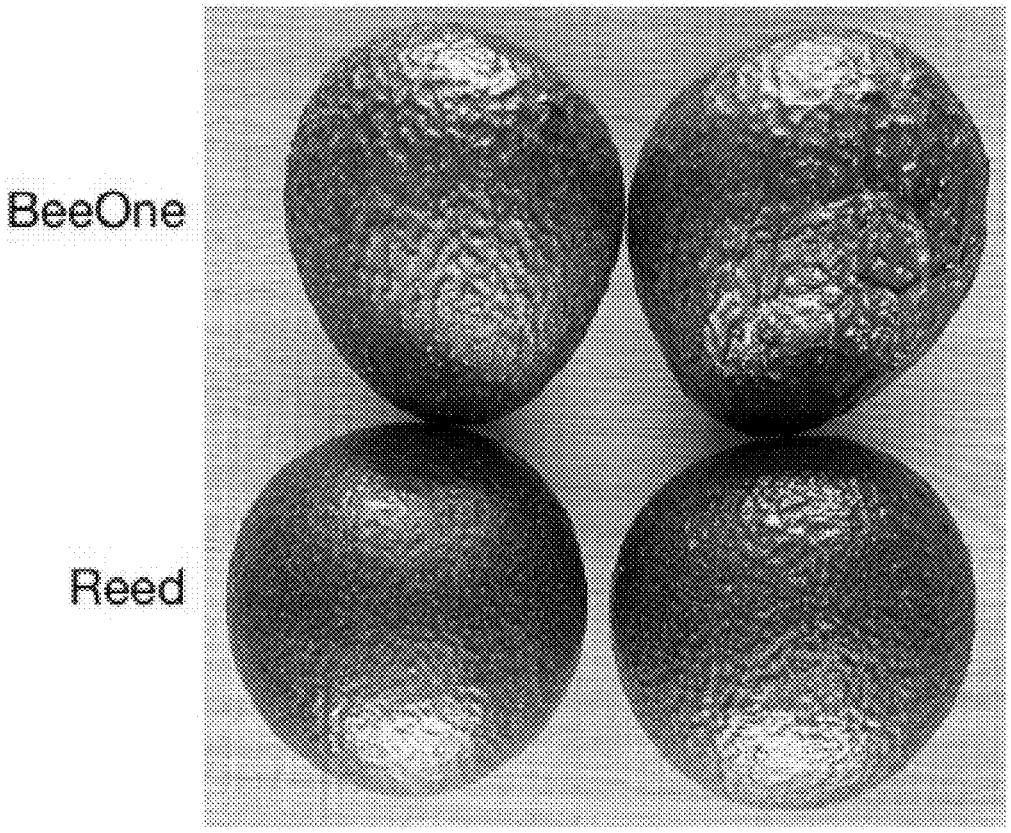
FIG. 1 is a colored photograph of a frontal view of a typical fruit of 'BeeOne' alongside the fruit of 'Reed'.
Figure 2:
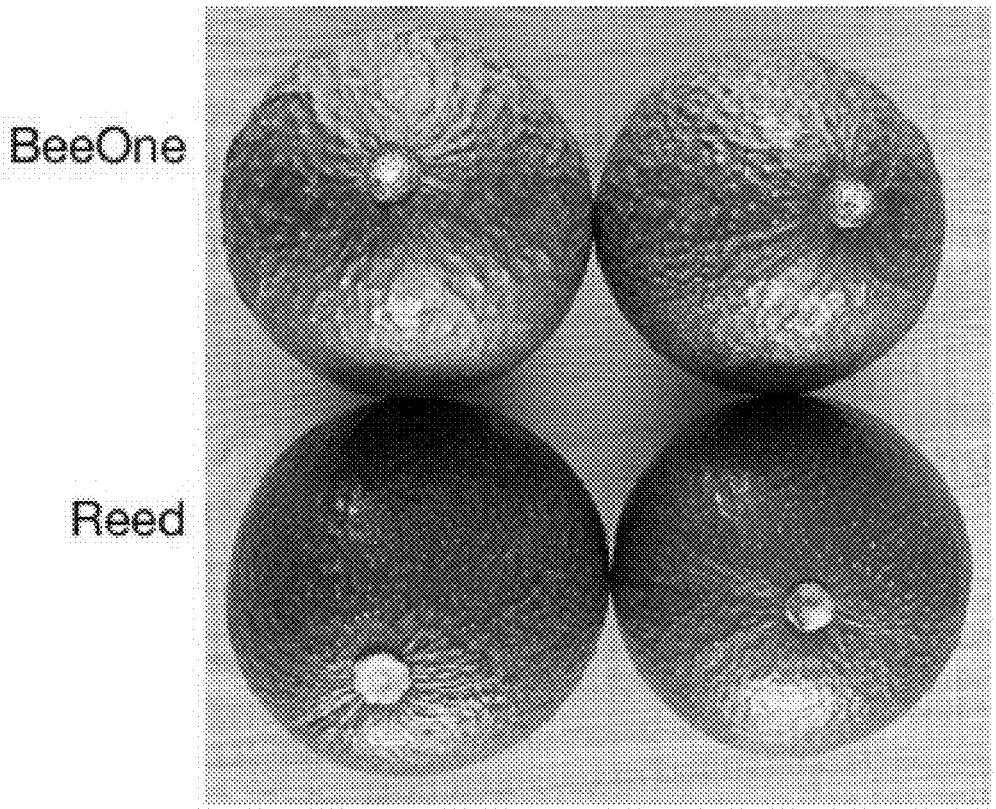
FIG. 2 is a colored photograph of a fruit stem end view of a typical fruit of 'BeeOne' alongside the fruit of 'Reed'.
Figure 3:
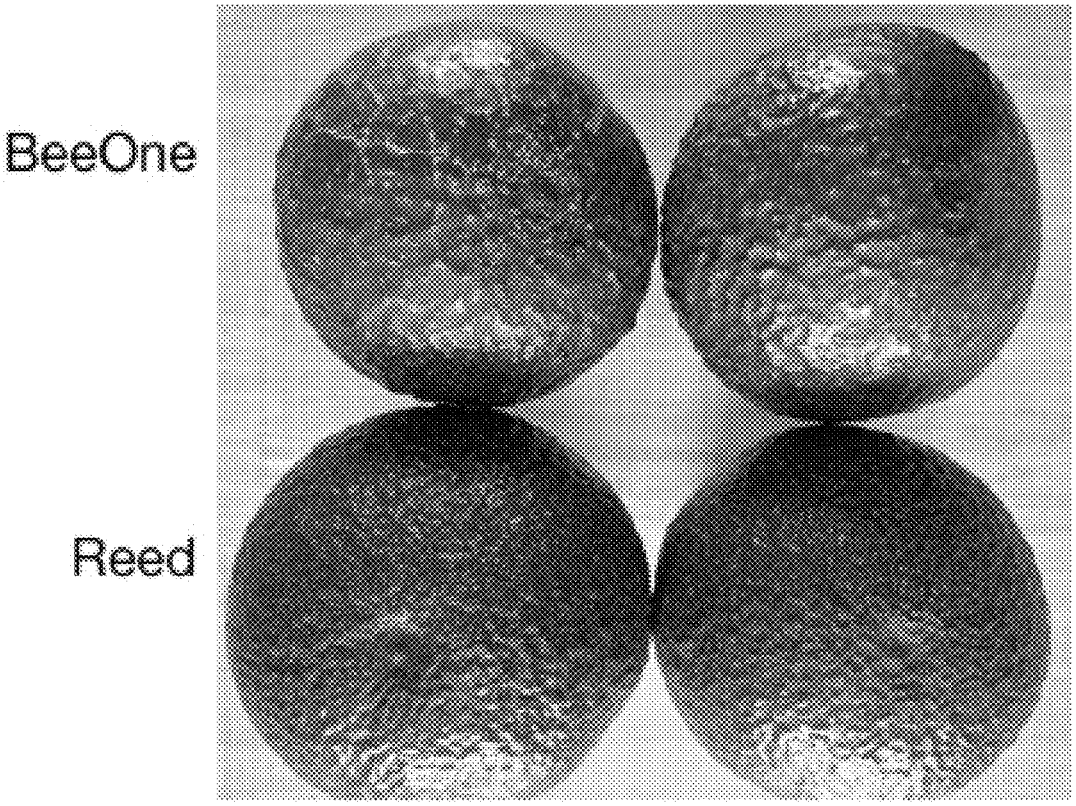
FIG. 3 is a colored photograph of a fruit distal end view of a typical fruit of 'BeeOne' alongside the fruit of 'Reed'.
Figure 4:
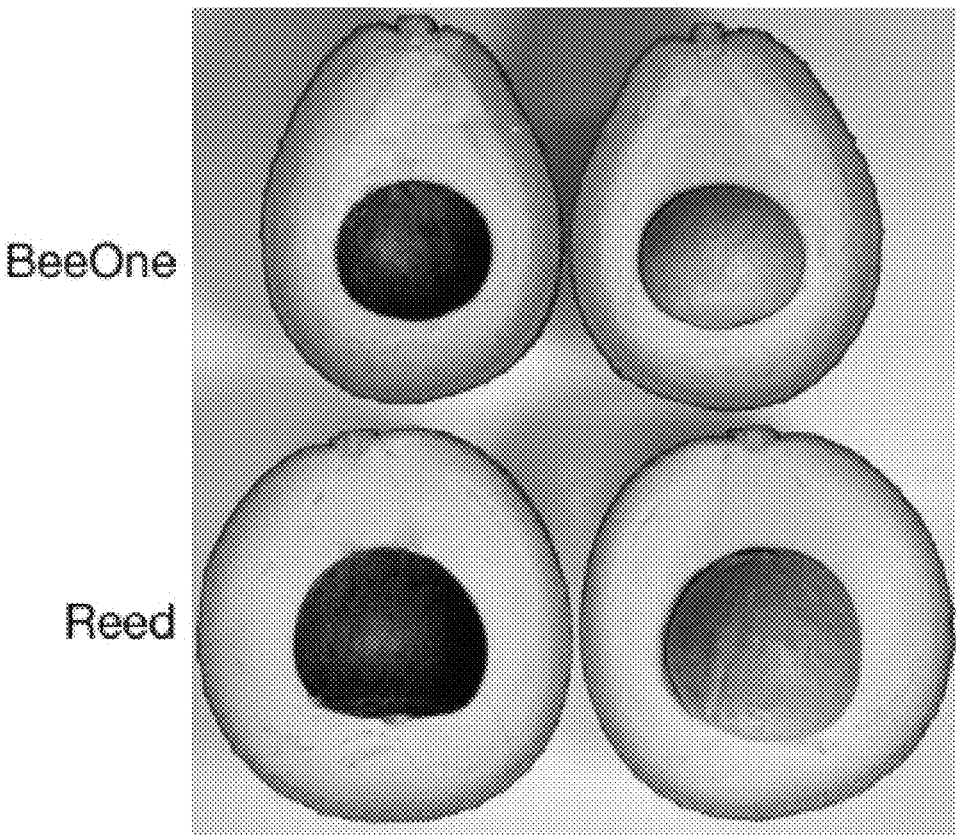
FIG. 4 is a colored photograph of a frontal view of a typical cut fruit of 'BeeOne' alongside the fruit of 'Reed' showing the pulp with and without seed respectively.
Figure 5:
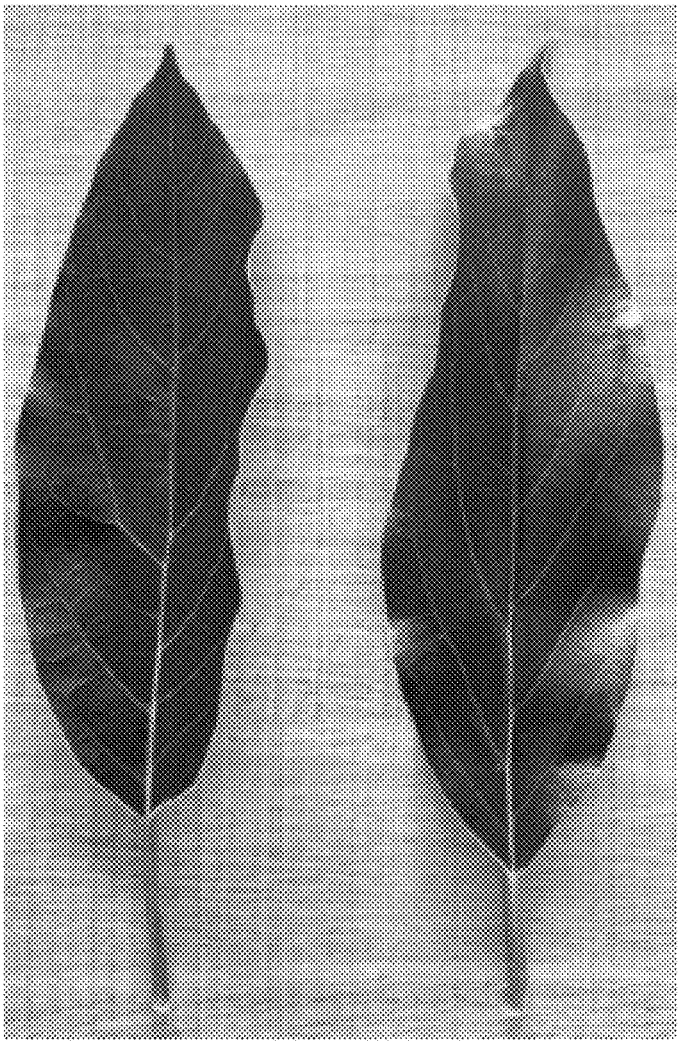
FIG. 5 is a frontal view of a leaf of 'BeeOne' alongside a leaf of 'Reed'.
Figure 6:
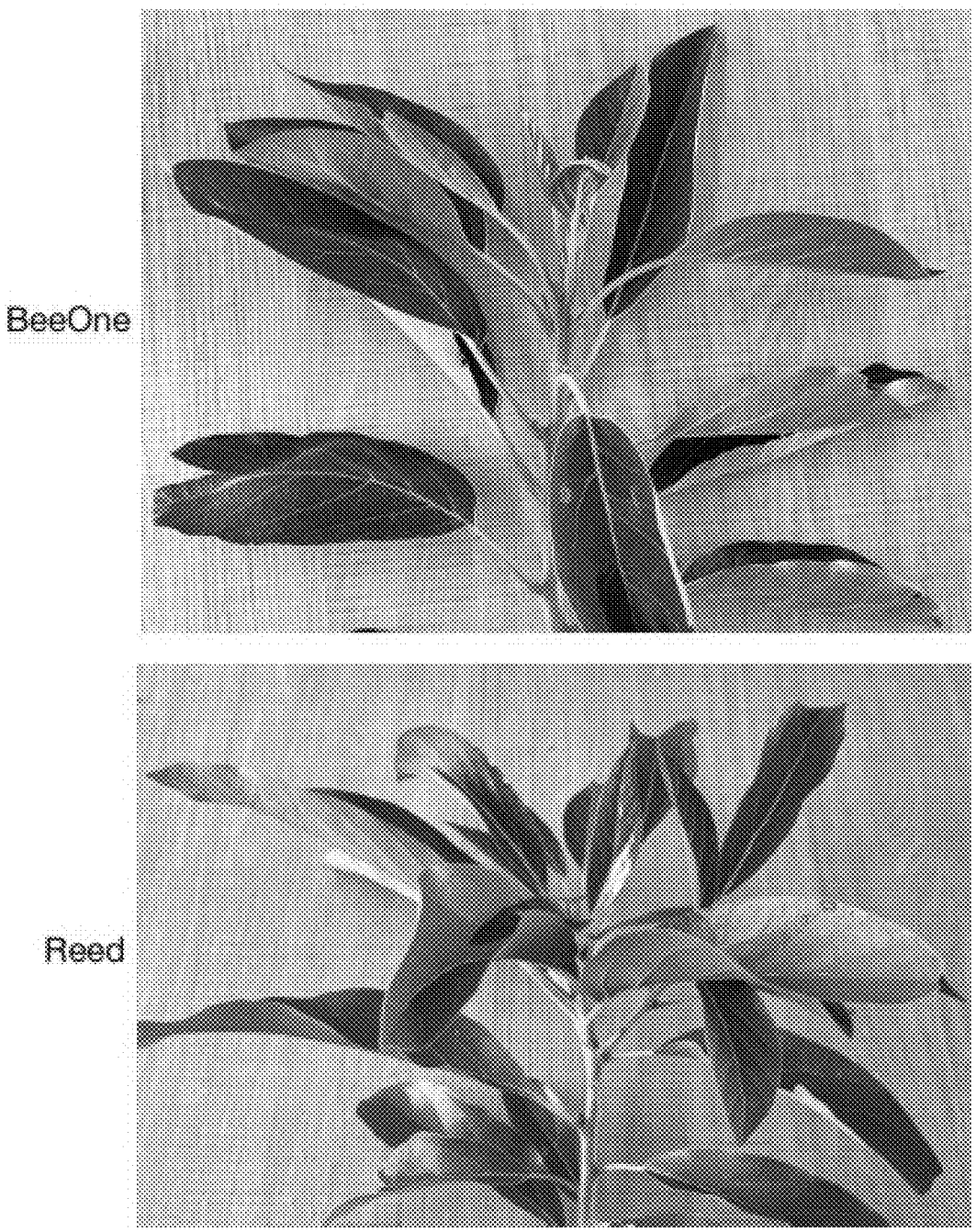
FIG. 6 is a frontal view of a leaf flush of 'BeeOne' alongside a leaf flush of 'Reed'.
Figure 7:
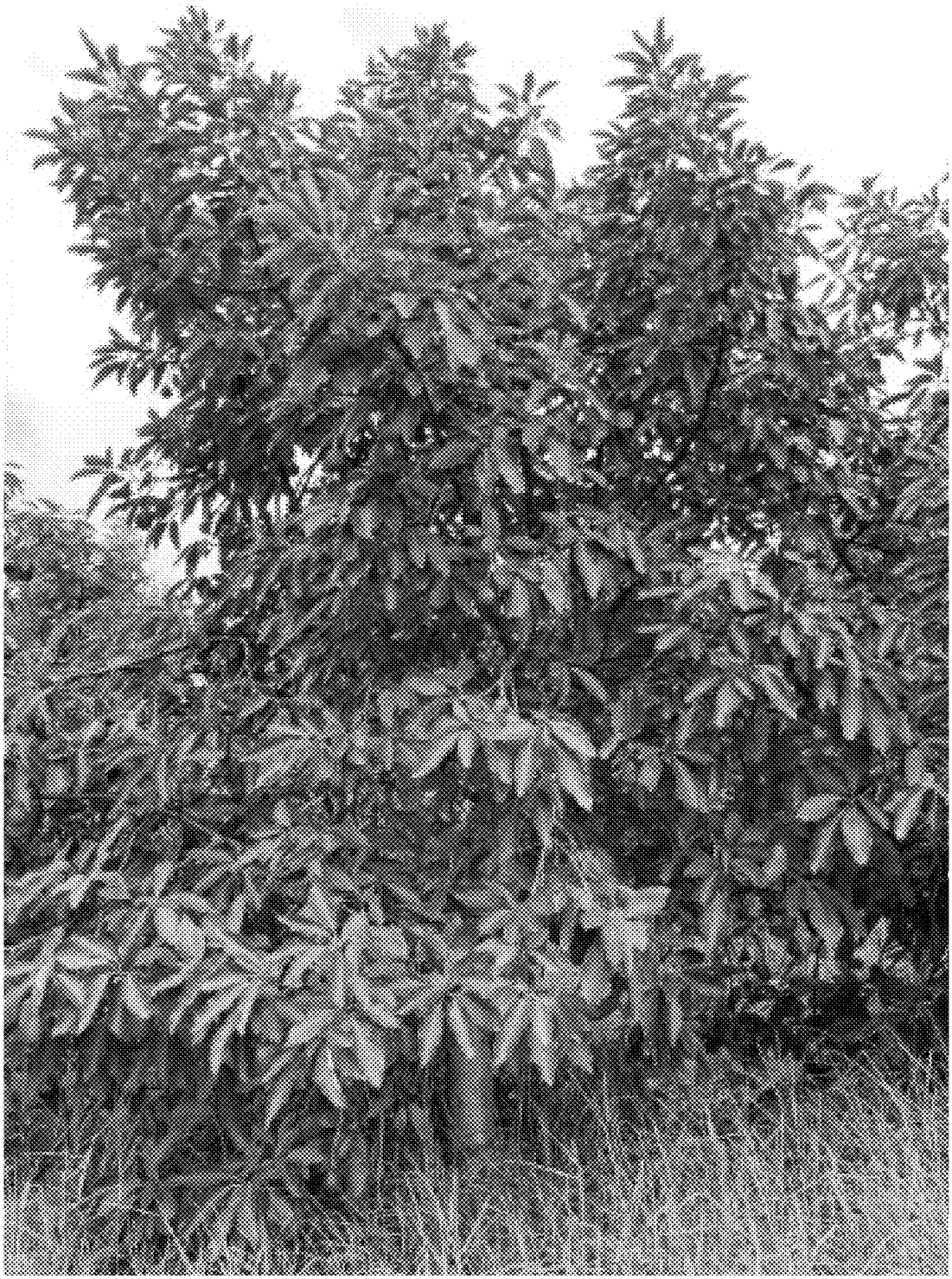
FIG. 7 is photograph of the 'BeeOne' tree to illustrate the typical tree shape.
Figure 8:
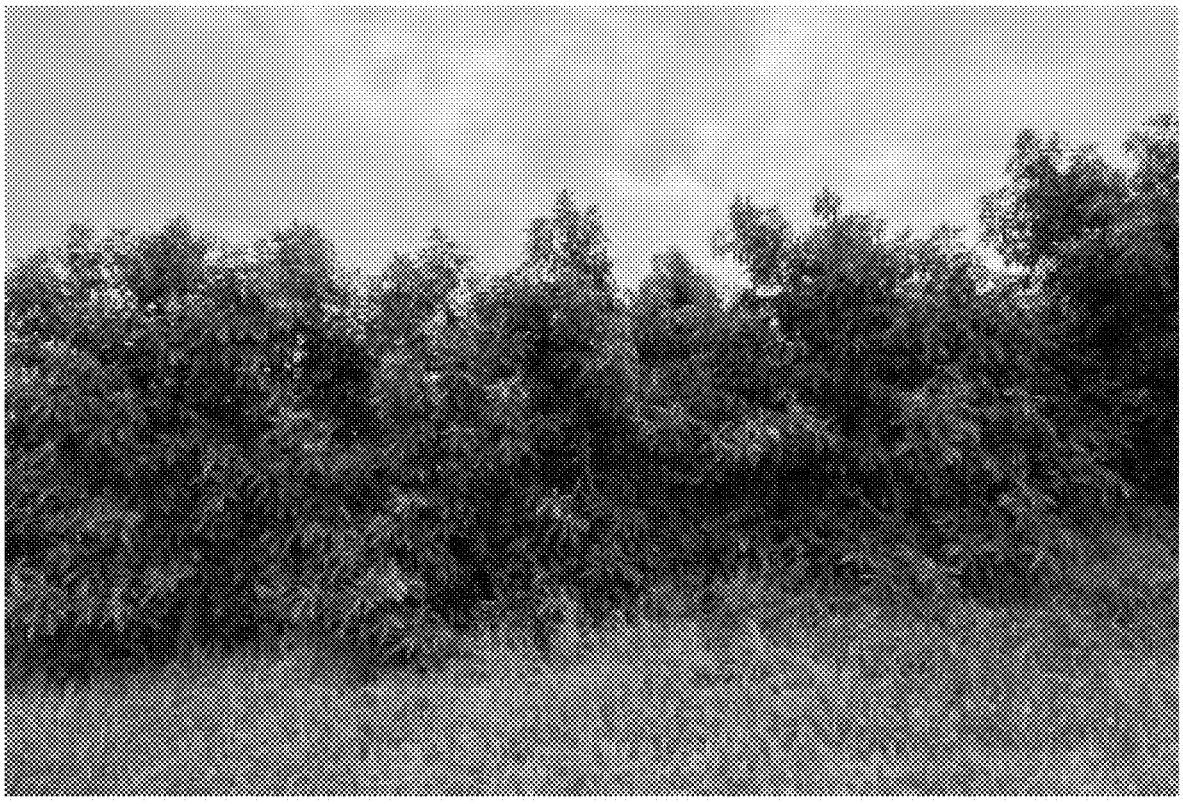
FIG. 8 is a photograph of a number of 'BeeOne' trees to illustrate the high density of trees planted in a 3 meter by 5 meter spacing.
Figure 9:
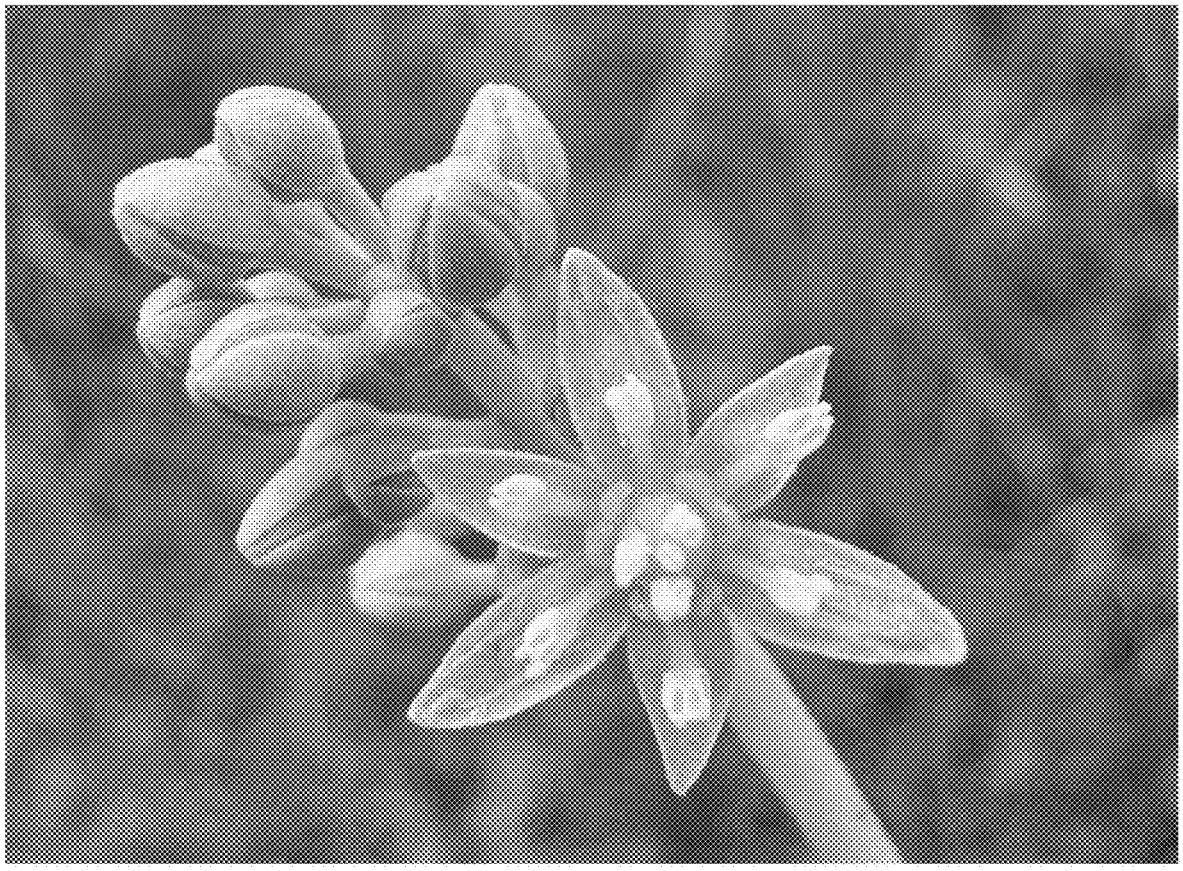
FIG. 9 is a photograph of a 'BeeOne' flower showing opening of the flower on the first day of opening with anthers pressed against flower petals.
Figure 10:
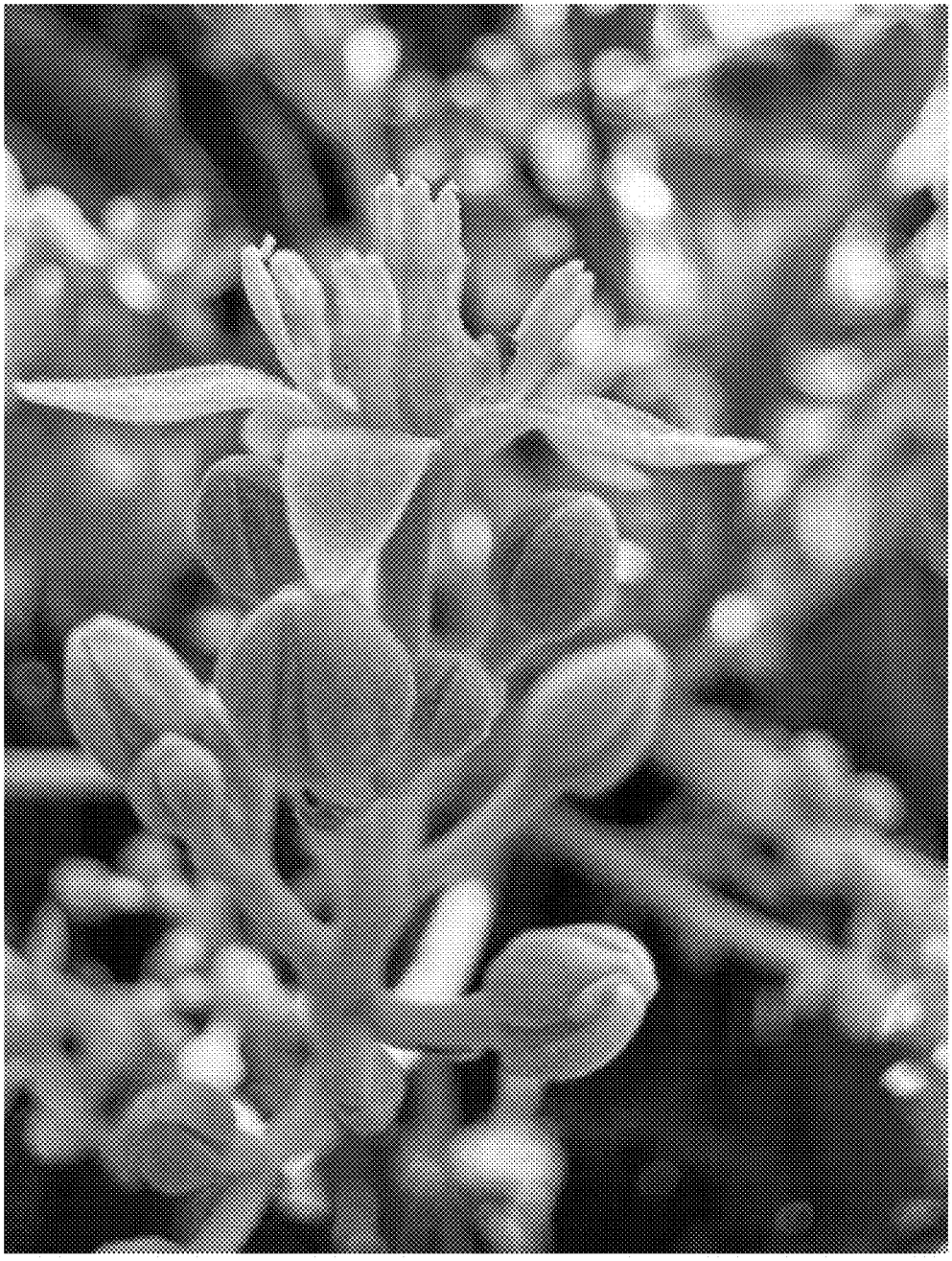
FIG. 10 is a photograph of a 'BeeOne' flower showing opening of the flower on the second day of opening with anthers raised around the pistil and pollen sack valves opening to release pollen.

The aforementioned drawings, following observations and measurements describe 'BeeOne' grown by the inventor at the premises of the applicant's farm in Leeukloof, Western Cape, Republic of South Africa during December 2023 to September 2024.

Tree general:

*Size*.—Medium. Approximately 4.5 meters in height. Trunk size average 48.5 cm in circumference when tree height is at 4.5 meters. Bark color is substantially identical to other commercial varieties like 'Reed' and 'Hass' (U.S. Plant Pat. No. 139) and light brown or gray, RHS Greyed-Green 197C in coloration. The bark on new wood is smooth, becoming corky on older wood, as with most avocado varieties.

*Form*.—The typical tree form or shape is upright to moderately spreading. This shape lends itself to high density plantings and interplanting.

*Branching habit*.—Moderately spreading with one 1-3 central leaders.

*Density*.—High density of trees can be planted in a 3 meter by 5 meter spacing.

Leaves:

*Young shoot/leaf*.—Color light green 144D with anthocyanin color sometimes present in very young flush leaves.

*Shape*.—Elliptic to oval with acute tip and acute base.

*Size*.—55-110 $cm^2$. Average length 17.1 cm; average width 7.3 cm.

*Weight*.—2.6 grams average.

*Bearing*.—Alternate.

*Margins*.—Slightly undulate.

*Surface texture*.—Upper leaf smooth waxy; lower leaf slightly leathery.

*Leaf blade anise aroma*.—None.

*Mature leaf color*.—Dark green near green group 139A with slightly glossy upper epidermis, and matte green underside near green group 137C.

*Petiole*.—Average length 4-6 cm, smooth surface texture, color light green 144D.

Flowers:

*Type*.—Mostly indeterminate cymose panicles of flowers opening in synchronous dichotomy of "Type B".

*Bud size*.—Individual flower buds average 8.1 millimeters (mm) in length. Flower buds are born on short pedicels 1-2 cm long on cymose panicles of 45-230 flowers.

*Inflorescence*.—Size: 9-16 cm, average 14 cm.

*Bud and panicle color*.—Near yellow-green group 151A.

*Petals*.—A total of 3, borne in a single whorl of three, slightly pubescent with entire margins with color near yellow green 151A.

*Sepals*.—A total of 3, borne in a single whorl of three, slightly pubescent with entire margins with color near yellow green 151A.

*Stamen*.—9 fertile stamens in 2 whorls, outer whorl of 6 stamens and inner whorl of 3 stamens each having 4 pollen chambers.

*Pistil*.—Simple, single pistil with one ovule in one carpel.

*Style*.—Straight.

*Nectaries*.—Sessile to stalked with 1 mm stalks.

*Pedicel*.—Pedicellate flower with 7.5 mm long pedicels with a thickness of 0.6 mm and a color near yellow-green group 151A.

*Opening*.—Synchronous dichotomy, single flowers opening twice over 2 consecutive days; female in the afternoon of day 1, and male in the morning of day 2 (B-flower type).

*Fertility*.—B-flower type with demonstrated strong/cross pollination of A-flower types.

*Blooming period*.—Extended, from late winter to end of spring.

Fruit:

*Date of first picking*.—Late-spring.

*Date of last picking*.—Mid-summer.

*Form/shape*.—Obovate.

*Base*.—Rounded.

*Apex*.—Rounded to truncate with an 30° offset flattened plane approximately 3-5 cm in diameter on the distal end which is often moderately russeted.

*Size*.—185 grams to 295 grams.

*Pedicel*.—Symmetrical, cylindrical thicker at fruit junction, pedicel nail absent, length 95-295 mm, 5-10 mm diameter, pebbled texture, yellow-green color 144D.

*Attachment*.—Centrally attached on highest point of fruit or may be slightly offset.

*Size*.—Generally smaller than 'Reed' variety and larger than 'Hass' (U.S. Plant Pat. No. 139) variety. Average length 136 mm. Average diameter 117 mm. Average weight 228 g.

*Color*.—Dark glossy green skin 135B with yellow-green 144D lenticels; becoming dark matte green 135B in late season and after ripening near green group 137A.

Flesh:

*Texture*.—Creamy.

*Fruit fibers*.—Slight in first crop, with none detected on subsequent crops.

*Eating quality*.—Excellent with similar flavor profile to 'Maluma' (U.S. Plant Pat. No. 21,099) and 'Reed'.

*Flavor*.—Good, with a slightly sweet creamy/nutty taste.

*Flesh to seed ratio*.—Excellent. Approximately 4.6:1.

*Color*.—Yellow-green 154C; with 3 mm yellow-green 144D layer adjacent to skin.

*Seed coat surface*.—Smooth to slightly wrinkled, becoming smooth to slightly wrinkled and papery when mature.

Skin:

*Thickness*.—Very thick. Approximately 1.8 mm.

*Surface*.—Highly pebbled texture with pronounced lenticels.

*Lenticels*.—Conspicuous, medium size, with yellow-green color 144D.

*Skin separation*.—Thick, does not separate from pulp by hand peeling, but pulp is easily scooped out with a spoon. Skin is thick, leathery, and not pliable similar to 'Reed' and unlike varieties 'Fuerte' or 'Harvest' U.S. Plant Pat. No. 14,238).

*Color*.—Dark glossy green 135B often with prominent yellow flecks 144D on lenticels.

Seed:

*Shape*.—Spheroid.

*Size*.—Average: Length 48 mm; width 45 mm.

*Weight*.—29.5 grams average.

*Color*.—Seed coat is dark brown greyed orange group 177A at maturity, with fleshy colored cotyledons in the near orange white group 159C.

*Productivity*.—Medium high, regular bearing. 140-240 fruit per tree with an average yield of 18150 kg/ha.

Uses: Fresh and processed fruit products.

Keeping quality: Long shelf life of 11 to 14 days; cut mid-season fruit shows slow oxidative browning in ambient air.

Shipping quality: Excellent with low incidents of post-harvest decay or softening when held at 5 degrees Celsius for 28 days.

Plant/fruit disease resistance/susceptibility: Not known. The variety is not genetically modified and has been tested to be free of avocado sunblotch viroid.

Plant hardiness or heat/cold resistance: The tree appears to have moderate heat and cold tolerance similar to that of 'Reed'.

The invention claimed is:

1. A new and distinct variety of *Persea americana* Mill. plant named 'BeeOne' as illustrated and described herein.

* * * * *

BeeOne Reed